(12) United States Patent
Liang et al.

(10) Patent No.: US 7,867,983 B2
(45) Date of Patent: Jan. 11, 2011

(54) METHODS TO PROTECT SKELETAL MUSCLE AGAINST INJURY

(75) Inventors: Bruce Tsan-Tang Liang, Avon, CT (US); Edward John Zambraski, Princeton, MA (US)

(73) Assignees: The University of Connecticut, Farmington, CT (US); The United States of America as represented by the Secretary of the Army, Washington, DC (US)

( * ) Notice: Subject to any disclaimer, the term of this patent is extended or adjusted under 35 U.S.C. 154(b) by 119 days.

(21) Appl. No.: 12/054,523

(22) Filed: Mar. 25, 2008

(65) Prior Publication Data

US 2008/0312180 A1 Dec. 18, 2008

Related U.S. Application Data

(60) Provisional application No. 60/920,834, filed on Mar. 29, 2007.

(51) Int. Cl.
*A01N 43/04* (2006.01)
*A61K 31/70* (2006.01)

(52) U.S. Cl. .............................. 514/45; 514/43; 514/46; 514/47; 514/48

(58) Field of Classification Search ........................ None
See application file for complete search history.

(56) References Cited

U.S. PATENT DOCUMENTS

2003/0092668 A1 5/2003 Liang et al.

FOREIGN PATENT DOCUMENTS

WO 2005003150 A2 1/2005

OTHER PUBLICATIONS

Jacobson et al. Apoptosis (1999), vol. 4, pp. 197-211.*
International Search Report and Written Opinion; International Application No. PCT/US2008/003937; International Filing Date Mar. 25, 2008; Applicant's File Reference UCT-0132-PCT (UCT0132US); Date of Mailing: Dec. 29, 2008; 22 pages.
Kilpatrick, et al.; "Adenosine A3 Agonist Cardioprotection in Isolated Rat and Rabbit Hearts is Blocked by the A1 Antagonist DPCPX"; Am. J. Physiol: Heart Circ. Physiol; 281; pp. H847-H853; (2001).
Lee, et al.; "Protective Effects of Renal Ischemic Preconditioning and Adenosine Pretreatment: Role of A1 and A3 Receptors"; Am. J. Physiol. Renal Physiol.; 278; pp. F380-F387; (2000).
Papanastasiou, et al.; "Protective Effect of Preconditioning and Adenosine Pretreatment in Experimental Skeletal Muscle Reperfusion Injury"; British Journal of Surgery; 86; pp. 916-922; (1999).
Rongen, et al.; "Annexin A5 Scintingraphy of Forearm as a Novel In Vivo Model of Skeletal Muscle Preconditioning in Humans"; Circulation; 111; pp. 173-178; (2005).
Schroeder, et al.; "Preconditioning with Ischemia or Adenosine Protects Skeletal Muscle from Ischemic Tissue Reperfusion Injury"; Journal of Surgical Research; 63; pp. 29-34; (1996).
Zatta, et al.; "Adenosine Receptor-Mediated Coronary Vascular Protection in Post-Ischemic Mouse Heart"; Life Sciences; 78; pp. 2426-2437; (2006).
Corrected International Search Report and Written Opinion; International Application No. PCT/US2008/003937; International Filling Date Mar. 25, 2008; Applicant's File Reference No. UCT0132US2; Date of Mailing Feb. 24, 2009; 18 pages.
Beyersdorf, et al; "Studies of Reperfusion Injury in Skeletal Muscle: Preserved Cellular Viability After Extended Periods of Warm Ischemia"; J. Cardiovasc. Surg.; 32; pp. 664-676; (1991).
Blaisdell; "The Pathophysiology of Skeletal Muscle Ischemia and the Reperfusion Syndrome: A Review"; Cardiovascular Surgery; 10; pp. 620-630; (2002).
Carroll, et al; "Acute Ischemic Preconditioning of Skeletal Muscle Prior to Flap Elevation"; Journal of the American Society of Plastic & Reconstructive Surgery; 100; pp. 58-65; (1997).
Duclos, et al; "Progressive Muscular Dystrophy in a-Sarcoglycan-Deficient Mice"; Journal of Cell Biology; 142; pp. 1461-1471; (1998).
Durbeej, et al; "Gene Transfer Establishes Primacy of Striated vs. Smooth Muscle Sarcoglycan Complex in Limb-Girdle Muscular Dystrophy"; Proc. Natl. Acad. Sci. USA; 100; pp. 8910-8915; (2003).
Pang, et al; "Effector Mechanism of Adenosine in Acute Ischemic Preconditioning of Skeletal Muscle Against Infarction"; American J. of Physiology; 42; pp. R887-R895; (1997).
Xu, et al; "IB-MECA and Cardioprotection"; Cardiovascular Drug Reviews; 24; pp. 227-238 (2006).
Zehng, et al; "A Novel Skeletal Muscle Cytoprotective Action of Adenosine A3 Receptors"; The FASEB Journal; 21; Abstract only; pp. 726.7; (2007).
Zheng, et al; "Protective Roles of Adenosine A1, A2A, and A3 Receptors in Skeletal Muscle Ischemia and Reperfusion Injury"; Am. J. Physiol. Heart Circ. Physiol.; 293; pp. H3685-H3691; (2007).

* cited by examiner

*Primary Examiner*—Patrick T Lewis
(74) *Attorney, Agent, or Firm*—Cantor Colburn LLP (57) ABSTRACT

Disclosed herein are compositions and methods for the treatment of skeletal muscle and/or the protection of skeletal muscle against injury. The adenosine $A_3$ receptor has been identified as a new therapeutic target for the treatment of skeletal muscle. Adenosine $A_3$ receptor agonists are used treat subjects with skeletal muscle ischemia and reperfusion (I/R) injuries, individuals with skeletal muscle disorders, and individuals suffering from skeletal muscle injury resulting from physical exertion.

21 Claims, 6 Drawing Sheets

METHODS TO PROTECT SKELETAL MUSCLE AGAINST INJURY

CROSS-REFERENCE TO RELATED APPLICATIONS

This application claims the benefit of U.S. Patent Application Ser. No. 60/920,834 filed on Mar. 29, 2007, which is incorporated by reference herein in its entirety.

STATEMENT REGARDING FEDERALLY SPONSORED RESEARCH & DEVELOPMENT

This invention was made with support from the United States Government under Grant #W81XWH-05-1-0060 from the Department of Defense. The U.S. Government has certain rights in the invention.

BACKGROUND

Ischemia and reperfusion can cause significant injury of skeletal muscle, which is a vulnerable tissue in the extremities. Trauma, autogenous skeletal muscle transplantation, surgical incision, vascular clamp application during vascular surgery or musculoskeletal reconstructive surgery, and sustained strenuous exertion can also induce skeletal muscle damage with deleterious systemic consequences. Protection of skeletal muscle from ischemia and reperfusion injury is therefore an important therapeutic goal. Although various measures including a tissue-preserving solution and cold immersion are used to preserve intact organs and skeletal muscle, a more effective method or pharmacological agents to protect skeletal muscle from ischemia/reperfusion injury is needed.

In addition, exercise, particularly strenuous exercise, can result in skeletal muscle injury. Skeletal muscle injury can result from over-activity and/or overload of the muscles and can result in impaired muscle function. At the present time, there is no effective pharmacological therapy that can protect the skeletal muscle from exertion-related injury. In addition, in subjects with degenerative muscle disease, there has not been an effective drug therapy that can ameliorate skeletal muscle injury. Thus, there is a need for methods and agents suitable for the treatment of skeletal muscle injury resulting from exercise.

BRIEF SUMMARY

In one embodiment, a method of treating skeletal muscle comprises administering to an individual in need of treatment for skeletal muscle injury an effective amount of an adenosine $A_3$ receptor agonist.

In another embodiment, a method of protecting skeletal muscle comprises administering to an individual in need of treatment for exertion-related skeletal muscle injury an effective amount of an adenosine $A_3$ receptor agonist.

In yet another embodiment, a method of preconditioning skeletal muscles from ischemia and reperfusion injury comprises administering to an individual in need of treatment for ischemia and reperfusion injury or for exertion-related skeletal muscle injury an effective amount of an adenosine $A_3$ receptor agonist.

BRIEF DESCRIPTION OF THE DRAWINGS

Referring now to the drawings wherein like elements are numbered alike in several figures.

The above-described and other features will be appreciated and understood by those skilled in the art from the following detailed description, drawings, and appended claims.

DETAILED DESCRIPTION

Disclosed herein are compositions and methods for the treatment of skeletal muscle and/or the protection of skeletal muscle against injury. The inventors herein have identified the adenosine $A_3$ receptor as a new therapeutic target for the treatment of skeletal muscle, as well as the class of adenosine $A_3$ receptor agonists as therapeutics for the treatment of skeletal muscle. The adenosine $A_3$ receptor agonists are used treat subjects with skeletal muscle ischemia and reperfusion (I/R) injuries, individuals with skeletal muscle disorders, and individuals suffering from skeletal muscle injury resulting from physical exertion. The adenosine $A_3$ receptor agonists, when administered via intra-peritoneal injection in a mouse model of I/R and exertion-induced injuries, have been demonstrated herein to decrease the extent of skeletal muscle injury.

Specifically, a mouse hindlimb ischemia/reperfusion injury model was used to demonstrate for the first time a novel anti-ischemic cytoprotective role of the adenosine $A_3$ receptor. Neutrophil infiltration and activation in the lungs can result from ischemia and reperfusion of skeletal muscle such as that of the hindlimb. Protection of skeletal muscle from ischemia and reperfusion injury is an important therapeutic goal in ameliorating both local and remote muscle and organ injury. A detailed and specific pharmacological characterization of both $A_1$ and $A_{2A}$ receptors was also carried out. A phospholipase C (PLC) $\beta2/\beta3$ knockout mice was used to determine the signaling role of phospholipase C in mediating the cytoprotective role of the adenosine receptor subtypes.

In addition, sustained strenuous exertion can induce skeletal muscle damage with deleterious consequences. Studies were undertaken to test the hypothesis that adenosine $A_3$ receptors represent a new target for the development of novel drugs that can reduce exertion-related skeletal muscle injury in not only normal subjects but also those with degenerative muscle diseases. Wild type, beta-sarcoglycan-deficient, and PLC$\beta2/\beta3$-null mice were used to determine the ability of adenosine $A_3$ receptor to protect skeletal muscles from exertion-induced skeletal muscle injury.

In one embodiment, a method of treating skeletal muscle comprises administering to an individual in need thereof an effective amount of an adenosine $A_3$ receptor agonist. As used herein, the term treating includes administration to an individual suffering from a skeletal muscle injury and administration preventatively or prophylactically to an individual at risk of skeletal muscle injury. Administration to an individual at risk of skeletal muscle injury can protect the skeletal muscle against injury. In one embodiment, the individual is at risk of, or has been diagnosed with, a skeletal muscle ischemia and reperfusion injury. Individuals in need of treatment include individuals having undergone or expected to undergo a surgical operation including those with skeletal muscle ischemia and reperfusion (I/R) injuries, individuals participating or expected to participate in exercise including strenuous exercise, including older individuals who may be more prone to skeletal muscle injury following physical exertion or ischemia and reperfusion; and individuals having diseases that affect skeletal muscle including degenerative muscle diseases such as inclusion body myositis, dystrophies (e.g., Duchenne, Becker, limb girdle, congenital, facioscapulohumeral, myotonic, oculopharyngeal, distal, and Emery-Dreifuss), and Amyotrophic Lateral Sclerosis (ALS). In one embodiment, wherein the individual has undergone, or is expected to undergo, a plastic, vascular (either an endovascular or an open bypass surgery), or reconstructive surgical operation where there is a risk of ischemia and reperfusion injury. In one embodiment, the individual is administered an adenosine $A_3$ receptor agonist to protect the skeletal muscle from exertion-related or ischemia and reperfusion injury. In another embodiment, the individual is a healthy individual. In another embodiment, the individual has a degenerative muscle disease.

In one embodiment, the adenosine $A_3$ receptor agonists are used to treat individuals in need of treatment for ischemia and reperfusion injury. Ischemia is a deficiency of oxygen in a part of the body causing metabolic changes, usually temporary, which can be due to a constriction or an obstruction in the blood vessel supplying that part. Reperfusion is the restoration of blood flow to an organ or tissue. Ischemia and reperfusion of the skeletal muscle can cause significant injury with deleterious consequences. Effective therapies that reduce such injury will have significant benefits in treatment of trauma, autogenous skeletal muscle transplantation, and vascular and musculoskeletal reconstructive surgery. As with anti-ischemic myocardial protection, adenosine and its receptors have been implicated in protecting the skeletal muscle against ischemia and reperfusion injury. The inventors herein have demonstrated for the first time that the adenosine $A_3$ receptor can induce potent cytoprotection of the skeletal muscle against ischemia and reperfusion injury. The adenosine $A_3$ receptor, but not the $A_1$ or $A_{2A}$ receptor, signals via phospholipase C $\beta2/\beta3$ to achieve its skeletal muscle protective effect.

In another embodiment, ischemic preconditioning with an adenosine $A_3$ receptor agonist can provide potent protection of the heart, as well as the skeletal muscles from ischemia/reperfusion injury. As with cytoprotection of the heart, extracellular adenosine is implicated in mediating the protective effect of preconditioning in skeletal muscle. Direct infusion of adenosine can mimic the effect of preconditioning in reducing skeletal muscle injury.

Adenosine is an important regulatory agent that exerts its cytoprotective effect via activation of its receptors. Activation of either adenosine $A_1$ or $A_3$ receptors can mediate potent anti-ischemic cardioprotective effect. The beneficial effect of the compositions and methods disclosed herein is novel in that it is achieved by a specific adenosine receptor subtype, the adenosine $A_3$ receptor. The unique advantage is that the adenosine $A_3$ receptor does not cause any hypotension or bradycardia in mammals. Although $A_1$ and $A_{2A}$ receptors can also exert a protective effect in the same model of I/R injury, both $A_1$ and $A_{2A}$ receptors can cause cardiodepression. Therefore, agents that act at the adenosine $A_3$ receptor are likely to have more favorable side effect profiles than drugs acting at the other receptors.

Exemplary adenosine $A_3$ receptor agonists include compounds according to general structures (I) and (II):

(I)

wherein each occurrence of X is N or CH; $R^1$ is aryl or —($C_1$-$C_3$ alkyl)-aryl wherein each aryl group is optionally substituted with 1, 2, or 3 substituents selected from halogen, $C_1$-$C_6$ alkyl, $C_1$-$C_6$ haloalkyl, —O($C_1$-$C_6$ alkyl), —O($C_1$-$C_6$ haloalkyl), —S($C_1$-$C_6$ alkyl), —S($C_1$-$C_6$ haloalkyl), —OH, —SH, nitro, or cyano; $R^2$ is hydrogen, $C_1$-$C_6$ alkyl, or $C_1$-$C_6$ haloalkyl; $R^3$ is hydrogen, halogen, $C_1$-$C_6$ alkyl, $C_1$-$C_6$ haloalkyl, —O($C_1$-$C_6$ alkyl), —O($C_1$-$C_6$ haloalkyl), —S($C_1$-$C_6$ alkyl), —S($C_1$-$C_6$ haloalkyl), —OH, or —SH; $R^4$ is hydrogen, halogen, $C_1$-$C_6$ alkyl, or $C_1$-$C_6$ haloalkyl; $R^5$ is —(C=O)$NR^7R^8$, —(C=S)$NR^7R^8$, —O(C=O)$NR^7R^8$, —$NR^9$(C=O)$NR^7R^8$, —O(C=S)$NR^7R^8$, or —$NR^9$(C=S)$NR^7R^8$ wherein $R^7$ is hydrogen, $C_1$-$C_6$ alkyl, or $C_1$-$C_6$ haloalkyl, $R^8$ is hydrogen, $C_1$-$C_6$ alkyl, or $C_1$-$C_6$ haloalkyl, or $R^7$ and $R^8$ combine to form a cyclic structure having 3, 4, or 5 carbons and 0, 1, or 2 heteroatoms of oxygen or $NR^{10}$, $R^{10}$ is hydrogen or $C_1$-$C_6$ alkyl, and $R^9$ is hydrogen or $C_1$-$C_6$ alkyl; and each occurrence of $R^6$ independently is hydrogen, $C_1$-$C_6$ alkyl, $C_1$-$C_6$ haloalkyl, or —(C=O)$C_1$-$C_6$ alkyl.

Specifically, the adenosine $A_3$ receptor agonists include compounds according to general structures (III) and (IV):

wherein X, $R^1$, $R^2$, $R^3$, $R^4$, $R^5$ and $R^6$ are defined above.

In one embodiment, the adenosine $A_3$ receptor agonist include those of general structures (I) to (IV) wherein X is N; $R^1$ is phenyl or benzyl wherein the phenyl or benzyl group is optionally substituted with 1, 2, or 3 substituents selected from halogen, $C_1$-$C_6$ alkyl, or $C_1$-$C_6$ haloalkyl; $R^2$ is hydrogen; $R^3$ is hydrogen or halogen; $R^4$ is hydrogen; $R^5$ is —(C=O)$NR^7R^8$, wherein $R^7$ is hydrogen, $C_1$-$C_6$ alkyl, or $C_1$-$C_6$ haloalkyl and $R^8$ is hydrogen; and $R^6$ is hydrogen.

Exemplary adenosine $A_3$ receptor agonists according to one of general structures (I) to (IV) include $N^6$-(3-iodobenzyl)adenosine-5'-N-methyluronamide ("IBMECA"); 2-chloro-$N^6$-(3-iodobenzyl)adenosine-5'-N-methyluronamide ("Cl-IBMECA"); (1'R,2'R,3'S,4'R,5'S)-4-{2-chloro-6-[(3-chlorophenylmethyl)amino]purin-9-yl}-1-(methylaminocarbonyl)bicyclo[3.1.0]hexane-2,3-diol ("MRS3558"); $N^6$-(3-chlorobenzyl)adenosine-5'-N-methyluronamide; 2-chloro-$N^6$-(3-chlorobenzyl)adenosine-5'-N-methyluronamide; $N^6$-(3-fluorobenzyl)adenosine-5'-N-methyluronamide; 2-chloro-$N^6$-(3-fluorobenzyl)adenosine-5'-N-methyluronamide; $N^6$-(3-methylbenzyl)adenosine-5'-N-methyluronamide; 2-chloro-$N^6$-(3-methylbenzyl)adenosine-5'-N-methyluronamide; $N^6$-(3-nitrobenzyl)adenosine-5'-N-methyluronamide; 2-chloro-$N^6$-(3-nitrobenzyl)adenosine-5'-N-methyluronamide; $N^6$-(3-cyanobenzyl)adenosine-5'-N-methyluronamide; 2-chloro-$N^6$-(3-cyanobenzyl)adenosine-5'-N-methyluronamide; $N^6$-(3,5-dichlorobenzyl)adenosine-5'-N-methyluronamide; 2-chloro-$N^6$-(3,5-dichlorobenzyl)adenosine-5'-N-methyluronamide; $N^6$-(3,5-diiodobenzyl)adenosine-5'-N-methyluronamide; 2-chloro-$N^6$-(3,5-diiodobenzyl)adenosine-5'-N-methyluronamide; $N^6$-(3,5-difluorobenzyl)adenosine-5'-N-methyluronamide; 2-chloro-$N^6$-(3,5-difluorobenzyl)adenosine-5'-N-methyluronamide; $N^6$-(3,5-dimethylbenzyl)adenosine-5'-N-methyluronamide; 2-chloro-$N^6$-(3,5-dimethylbenzyl)adenosine-5'-N-methyluronamide; $N^6$-(3-iodophenyl)adenosine-5'-N-methyluronamide; 2-chloro-$N^6$-(3-iodophenyl)adenosine-5'-N-methyluronamide; $N^6$-(3-chlorophenyl)adenosine-5'-N-methyluronamide; 2-chloro-$N^6$-(3-chlorophenyl)adenosine-5'-N-methyluronamide; $N^6$-(3-fluorophenyl)adenosine-5'-N-methyluronamide; 2-chloro-$N^6$-(3-fluorophenyl)adenosine-5'-N-methyluronamide; $N^6$-(3-methylphenyl)adenosine-5'-N-methyluronamide; 2-chloro-$N^6$-(3-methylphenyl)adenosine-5'-N-methyluronamide; $N^6$-(3-nitrophenyl)adenosine-5'-N-methyluronamide; 2-chloro-$N^6$-(3-nitrophenyl)adenosine-5'-N-methyluronamide; $N^6$-(3-cyanophenyl)adenosine-5'-N-methyluronamide; 2-chloro-$N^6$-(3-cyanophenyl)adenosine-5'-N-methyluronamide; $N^6$-(3,5-dichlorophenyl)adenosine-5'-N-methyluronamide; 2-chloro-$N^6$-(3,5-dichlorophenyl)adenosine-5'-N-methyluronamide; $N^6$-(3,5-diiodophenyl)adenosine-5'-N-methyluronamide; 2-chloro-$N^6$-(3,5-diiodophenyl)adenosine-5'-N-methyluronamide; $N^6$-(3,5-difluorophenyl)adenosine-5'-N-methyluronamide; 2-chloro-$N^6$-(3,5-difluorophenyl)adenosine-5'-N-methyluronamide; $N^6$-(3,5-dimethylphenyl)adenosine-5'-N-methyluronamide; 2-chloro-$N^6$-(3,5-dimethylphenyl)adenosine-5'-N-methyluronamide.

In one embodiment, the adenosine $A_3$ receptor agonist is combined with an adenosine $A_1$ receptor agonist, an adenosine $A_{2A}$ receptor agonist, or a combination comprising one or more of the foregoing agonists. Exemplary adenosine $A_1$ receptor agonists include CCPA. Exemplary adenosine $A_{2A}$ receptor agonists include CGS21680.

Disclosed herein are compositions and methods for the treatment of skeletal muscle and/or the protection of skeletal muscle against injury. Several agonists/antagonists of adenosine $A_1$, $A_{2A}$, and $A_3$ receptors have been identified. CCPA is highly $A_1$ receptor-selective agonist; DPCPX is an $A_1$ receptor-selective antagonist; MRS1191 is an $A_3$ receptor-selective antagonist; Cl-IBMECA is an $A_3$ receptor-selective agonist; CGS21680 is an $A_{2A}$ receptor agonist; and SCH 442416 is an $A_{2A}$ receptor antagonist.

Several lines of evidence clearly delineate the cytoprotective role of adenosine $A_1$, $A_{2A}$, and $A_3$ receptors. The highly $A_1$ receptor-selective agonist CCPA decreased skeletal muscle ischemia and reperfusion injury. The protective effect was blocked only by the $A_1$ receptor-selective antagonist DPCPX, but not by the $A_3$ receptor-selective antagonist MRS1191. Conversely, the $A_3$ receptor-selective agonist Cl-IBMECA reduced skeletal muscle injury, and this protective effect, although insensitive to blockade by the $A_1$ receptor antagonist DPCPX, was completely abrogated by the $A_3$ receptor antagonist MRS1191, which was shown to antagonize the adenosine $A_3$ receptor in mice. Similarly, the cytoprotective effect of $A_{2A}$ receptor agonist CGS21680 was selectively blocked by its antagonist SCH 442416 and was insensitive to the $A_3$ antagonist MRS1191. The $A_1$ antagonist DPCPX, at the current dosage, was able to attenuate the CGS21680-induced skeletal muscle protection. Several explanations are possible. Given the interaction between $A_1$ and $A_{2A}$ receptors, it is possible that $A_{2A}$ receptor-mediated effect could be potentiated by $A_1$ receptor activation. A positive interaction between adenosine $A_1$ and $A_{2A}$ receptors was recently demonstrated in rat heart. Since DPCPX could inhibit the protective effect of CGS21680 in the current skeletal muscle ischemia/reperfusion injury model, it is possible that $A_1$ receptor activation contributed to the CGS21680-induced skeletal muscle protection. Recent evidence suggests that protein kinase C (PKC) activation can potentiate the adenosine $A_{2B}$ receptor signaling during reperfusion in the heart. Thus, another possible explanation is that PKC activation, induced by adenosine $A_1$ receptor, may also increase the responsiveness of the adenosine $A_{2A}$ receptor signaling during reperfusion in skeletal muscle. Overall, the present data provided detailed characterization of antagonists and agonists associated with $A_1$, $A_{2A}$, and $A_3$ receptors in the current in vivo model of skeletal muscle ischemia/reperfusion injury. The study confirms their selectivity at each adenosine receptor subtype and indicate that the cytoprotection afforded by each receptor agonist is due to activation of that specific receptor.

PLC β2/β3 deficiency selectively abrogated the protective effect of $A_3$ receptor agonist Cl-IBMECA and had no effect on CCPA- or CGS21680-induced protection. It was unlikely that PLC β2/β3 deficiency affected the bioavailability or pharmacokinetic properties of Cl-IBMECA for the following reason. CCPA and CGS21680 have similar size and molecular weights as Cl-IBMECA. Both CCPA and CGS21680 were fully capable of protecting against skeletal muscle injury in the PLC β2/β3 knockout mice. In WT mice, CGS21680 induced anti-ischemic skeletal muscle protection in a manner that was insensitive to blockade by either DPCPX or MRS1191, but was completely abolished by the $A_{2A}$ receptor-selective antagonist SCH 442416. The protective effect of CGS21680 remained unaffected and intact in PLC β2/β3-null mice.

While PLC β2/β3 is not involved in mediating the protective effect of $A_1$ or $A_{2A}$ receptors in the skeletal muscle, ATP-sensitive $K^+$ channels appear to be an important effector mechanism for the anti-ischemic effect of the $A_1$ receptor. The adenosine $A_{2A}$ receptor serves an important nonredundant role in suppressing immune and lymphoid cells and thus in protecting against inflammatory tissue damage. Since activation of adenosine $A_{2A}$ receptors on $CD4^+$ T cells mediated potent protection against renal ischemia/reperfusion injury, it is possible that the same mechanism is also responsible for its protection in the skeletal muscle in vivo. Activation of the $A_3$ receptor in rodent immune cells such as mast cells is proinflammatory and may be damaging. Genetic absence or antagonism of adenosine $A_3$ receptors augmented an increase in coronary flow or hypotension mediated by adenosine or an $A_{2A}$ receptor agonist, pointing to a vasoconstrictive role of the vascular $A_3$ receptor. Activated mast cells and neutrophils mediate skeletal muscle ischemia/reperfusion injury. The present data could not determine whether the adenosine $A_3$ receptor-mediated protection was due to direct activation of $A_3$ receptors on the skeletal muscle or the result of an anti-inflammatory action of $A_3$ receptors on the immune cells. EBD is a dye that accumulates in injured tissues as a result of an increase in vascular permeability and a disruption of sarcolemmal integrity of the tissue (such as muscle) supplied by the vasculature. Without being held to theory, it is possible that a decrease in EBD staining was due to a decrease in vascular permeability induced by one or all of the adenosine receptor subtypes studied. Differentiating a protective effect of adenosine receptor subtypes at the levels of vasculature, circulating immune cells, and skeletal muscle may resolve some of these effects. Bone marrow transplant from adenosine receptor knockout mice, or possible creation of vascular or skeletal muscle specific knockout of adenosine receptor subtypes should provide a more definitive answer to this question.

That the adenosine $A_3$ receptor exerts a potent cytoprotective effect in mouse skeletal muscle is consistent with its cardioprotective action in the mouse heart. While PLC is currently shown to have an important role in mediating the $A_3$ effect in skeletal muscle, a previous study suggested that PLD, but not PLC, mediated the cardioprotective effect of adenosine $A_3$ receptors in chick embryo ventricular myocytes. The reasons for this apparent difference are not clear; however, several plausible explanations are offered. First, species and age differences (chick embryos vs. adult mouse) may be important. Second, the coupling of adenosine $A_3$ receptors to PLC vs. PLD may be different in skeletal than in cardiac muscles. Third, the skeletal muscle ischemia/reperfusion injury preparation was an in vivo and intact animal model, whereas the model used previously was an isolated cell culture model. The present gene knockout approach rendered all cells completely deficient in PLC β2/β3 including skeletal muscle and circulating immune cells capable of mediating anti- and pro-inflammatory. Without being held to theory, it is possible that PLC mediated an anti-inflammatory effect of $A_3$ receptors on circulating immune cells. In this scenario, knockout of PLC would eliminate the anti-inflammatory effect of $A_3$ receptors on immune cells and thus abrogated their cytoprotective effect on skeletal muscles.

The combined use of receptor pharmacological tools and a gene ablation approach delineated, for the first time, a distinct anti-ischemic protective role of adenosine $A_1$, $A_{2A}$, and $A_3$ receptor subtypes in skeletal muscle. Although both adenosine $A_1$ and $A_{2A}$ receptors have shown anti-ischemic protective properties, agonists at either receptor caused pronounced decreases in blood pressure or heart rate. The data shown herein provide convincing evidence that the adenosine $A_3$ receptor is a novel cytoprotective receptor in skeletal muscle. Because the $A_3$ receptor agonist is not associated with cardiac or hemodynamic depression, the $A_3$ receptor represents a potential therapeutic target because of its ability to ameliorate skeletal muscle injury.

In one embodiment, included herein is a composition comprising an $A_3$ receptor agonist and a pharmaceutically acceptable excipient.

For oral administration, the pharmaceutical preparation can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well-known in the art.

Preparations for oral administration can be suitably formulated to give controlled release of the active compound.

For buccal administration, the compositions can take the form of tablets or lozenges formulated in conventional manner.

For administration by inhalation, the compositions are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion via either intravenous, intraperitoneal or subcutaneous injection. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compositions can be formulated into creams, lotions, ointments or tinctures, e.g., containing conventional bases, such as hydrocarbons, petrolatum, lanolin, waxes, glycerin, or alcohol. The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (e.g., subcutaneously or intramuscularly) or by intramuscular injection. Thus, for example, the compositions can be formulated with suitable polymeric or hydrophobic materials (e.g., as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions can, if desired, be presented in a pack or dispenser device, which can contain one or more unit dosage forms containing the active ingredient. The pack can for example comprise metal or plastic foil, such as a blister pack. The pack or dispenser device can be accompanied by instructions for administration.

The amount of the $A_3$ receptor agonist that may be combined with pharmaceutically acceptable excipients to produce a single dosage form will vary depending upon the host treated and the particular mode of administration. The specific therapeutically effective amount for a particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the compounds described herein found in therapeutic compositions will vary depending upon a number of factors, including the dosage of the drug to be administered, the chemical characteristics (e.g., hydrophobicity) of the compounds employed, and the route of administration. In general terms, the $A_3$ receptor agonist may be provided in an aqueous physiological buffer solution (for example, 1 cc) containing about 0.2% w/v compound for oral administration. Exemplary dose ranges are about 200 µg/kg of body weight per day in three divided doses; a specific dose range is about 200 µg/kg to about 1000 µg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors.

The disclosure is further illustrated by the following non-limiting examples.

Materials and Methods

Mouse Hindlimb Ischemia and Reperfusion Model: After 2.5- to 3-month-old wild-type (WT; C57BL6 strain) or PLC β2/β3 knockout mice (in C57BL6 background), each weighing about 23-25 g, were sedated with anesthetic (pentobarbital 50 mg/kg was given by intraperitoneal [i.p.] injection), their right or left hindlimbs (used randomly) were elevated briefly to minimize retained blood before being subjected to ischemia. Ischemia was induced by placement of a constrictor band (Latex O-Rings, Miltex Instruments, York, Pa.) above the greater trochanter with a McGiveney Hemorrhoidal Ligator (7 in long; Miltex). After 90 minutes of warm ischemia at 37° C., the constrictor was removed to allow reperfusion for 24 hours. The mice were continuously maintained on a 37° C. warming pad (Physitemp Instruments Inc, Clifton, N.J.) during the reperfusion. After the mice were killed by anesthetic overdose, the gastrocnemius muscle was quickly frozen, cut into three slices separated by 2-3 mm, and embedded in Shandon Cryomatrix (polyvinyl alcohol 10%, polyethylene glycol 4%; Anatomical Pathology U.S.A., Pittsburgh, Pa.). Each slice was processed as one 10 µm section on a Thermo Electron/Shandon Cryotome (Anatomical Pathology), fixed in ice-cold acetone, air dried, and washed in phosphate-buffered saline (PBS). Each 10 µm section had seven fields.

Gastrocnemius was used because of its high proportion of fast-twitch muscle, which is prone to ischemia and reperfusion injury.

Quantification of Skeletal Muscle Injury: Evans Blue dye (EBD), prepared as a 1% wt/vol solution to yielding 1 mg of EBD/10 g body weight), was given via a separate i.p. injection 2.5 hours before the induction of ischemia. EBD stained only injured muscle and EBD-positive cells were quantified. The percent EBD-positive cells in each field was averaged with those from all seven fields within one 10 μm section. The averaged fraction of EBD-positive cells in each 10 μm section was similar among the three sections. Each 10 μm section was also stained with rabbit polyclonal anti-skeletal muscle actin antibodies (ab15265; Abcam Inc, Cambridge, Mass.) and goat polyclonal anti-rabbit IgG conjugated with fluorescein isothiocyanate. Sections were mounted, and their cross sections were viewed with fluorescent microscopy (Evans Blue dye [EBD]-positive cells via a DM580 band pass filter 510-560 nm with emission of 590 nm; fluorescein isothiocyanate cells via a DM510 filter of 450-490 nm with emission at 520 nm). Each field was counted at 20× magnification and their images captured via the two filters for quantification of muscle injury as follows. Images were acquired and stored as JPEG files with a Macrofire camera (Macrofire 1.0, Optronics, Goleta, Calif.). The ImageProPlus Program (version 5.0, Media Cybernetics, Inc, Silver Spring, Md.) was used for the quantitative determination. The percentage of EBD-positive areas was calculated by dividing the area of EBD staining by the total muscle cells, a quantity defined as the total area stained by anti-skeletal muscle actin antibodies and was identical to the total area in each field minus the area not occupied by any cell. The actin-stained area included EBD-positive area, as shown in superimposed EBD- and actin antibody-stained images. Serum creatine kinase (CK) activity was measured with a previously described procedure. The fraction of skeletal muscle staining positive for EBD represented a direct determination of the muscle that was injured, and the serum CK level provided a circulating index of the extent of skeletal muscle injury. Both are established and accepted methods to quantify skeletal muscle injury.

Protocol for Administration of Adenosine Receptor Agonist and Antagonist. Adenosine receptor agonists (0.07 mg/kg for Cl-IBMECA and CGS21680, 0.05 mg/kg for CCPA and R-PIA), antagonists (0.2 mg/kg for DPCPX, 0.05 mg/kg for 3-ethyl 5-benzyl-2-methyl-6-phenyl-4-phenylethynyl-1,4-(±)-dihydropyridine-3,5-dicarboxylate (MRS1191), 0.017 mg/kg for SCH 442416), or vehicle (0.1% DMSO in PBS) was administered in a sterile 0.1-ml volume by i.p. injection 2 hours before induction rather than at the onset of ischemia. This protocol allowed time for absorption of adenosine ligands and for their presence in circulation before the beginning of ischemia. Previous studies demonstrated that i.p. injection of similar doses of adenosine receptor agonists produced potent pharmacological myocardial protection in the mouse. Similar i.p. doses of adenosine receptor antagonists (MRS1191 and DPCPX) were also given, and only MRS1191 blocked the myocardial protection afforded by the $A_3$ receptor agonist Cl-IB-MECA (41). When both antagonist and agonist were administered, the antagonist was given 30 min before the agonist. Unless otherwise indicated, data are shown as mean±standard error (SE). One-way ANOVA followed by posttest Newman-Keuls comparison was used to analyze the statistical significance of differences in more than two groups. P<0.05 was considered statistically significant.

Materials and Chemicals: The adenosine receptor ligands DPCPX, MRS1191, 2-p-(2-Carboxyethyl)phenethylamino-5'-N-ethylcarboxamidoadenosine (CGS21680), 2-chloro-$N^6$-cyclopentyladenosine (CCPA), 2-chloro-$N^6$-(3-iodobenzyl)adenosine-5'-N-methyluronamide (Cl-IBMECA), and R-PIA were obtained from Sigma Chemicals (St. Louis, Mo.). The adenosine $A_{2A}$ receptor antagonist 2-(2-Furanyl)-7-[3-(4-methoxyphenyl)propyl]-7H-pyrazolo[4,3-e][1,2,4]triazolo[1,5-C]pyrimidin-5-amine (SCH 442416) was from TOCRIS Bioscience (Ellisville, Mo.).

PLC β2/β3-Deficient Mice: PLC β2/β3-null mice were bred as previously described. C57BL6 mice were obtained from Jackson Laboratories (Bar Harbor, Me.). All animal experiments were conducted under the guidelines on humane use and care of laboratory animals for research and approved by the Institutional Animal Care and Use Committee of the University of Connecticut Health Center.

EXAMPLE 1

Role of Adenosine $A_1$ Receptors in Anti-ischemic Skeletal Muscle Protection

Figure 1:
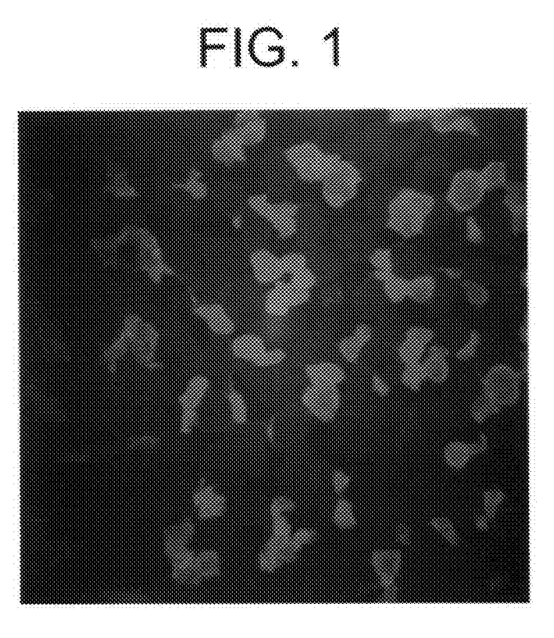
FIG. 1 is shows the extent of EBD (Evans Blue dye) staining in mice treated with vehicle (0.1% DMSO in phosphate-buffered saline, pH 7.4, n=7 mice). The contralateral leg not subjected to ischemia-reperfusion showed no EBD uptake.
Figure 2:
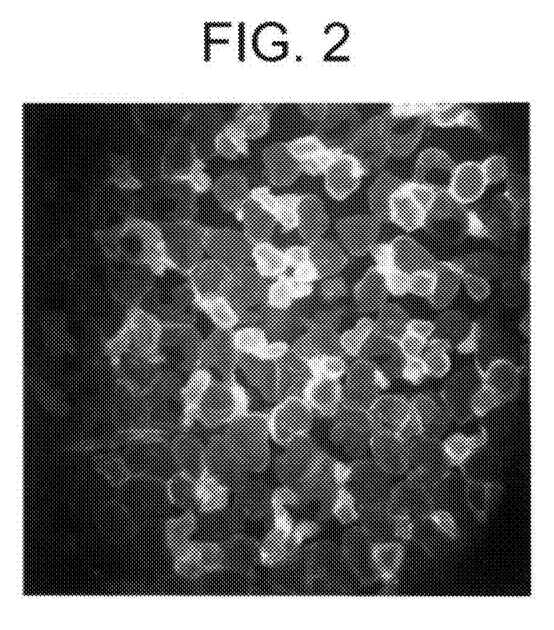
FIG. 2 shows the same section stained with rabbit polyclonal anti-skeletal muscle actin antibodies followed by staining with goat anti-rabbit IgG conjugated with fluorescein isothiocyanate.

Ischemia followed by reperfusion resulted in significant limb skeletal muscle injury in PBS vehicle-treated mice. The extent of injury was quantified by an increase in the EBD staining of the skeletal myocytes (FIG. 1). The fraction of total skeletal muscle cross sections that stained positive for EBD was 28%±6% (n=7 mice, SE, FIG. 1). Administration of the relatively nonselective adenosine receptor agonist R-PIA prior to ischemia and reperfusion caused a significant reduction in the extent of injury (FIG. 2). To elucidate the cytoprotective role of different adenosine receptor subtypes, it was found that a highly $A_1$ receptor-selective agonist, CCPA, induced a large decrease in the extent of muscle injury (FIG. 3; EBD-positive area in CCPA-treated mice: 10.8%±2%, n=12 mice, vs. PBS vehicle-treated mice: 28%±6%, n=7 mice, P<0.05). The $A_1$ receptor-selective antagonist DPCPX completely abrogated the cytoprotective response to CCPA (FIG. 3; DPCPX and CCPA treatment: 22%±3.3%, n=9 mice, P<0.05 vs. CCPA treatment). The adenosine $A_3$ receptor-selective antagonist MRS1191 did not affect CCPA-mediated protection (FIG. 3; MRS1191 and CCPA treatment: 12.2%±2.4%, n=23 mice, P>0.05 vs. CCPA treatment), indicating that the adenosine $A_1$ receptor protects skeletal muscle from ischemia/reperfusion injury. The contralateral limb not subjected to ischemia/reperfusion showed no EBD staining (data not shown), indicating absence of muscle injury in the non-ischemic limb.

EXAMPLE 2

Figure 4:
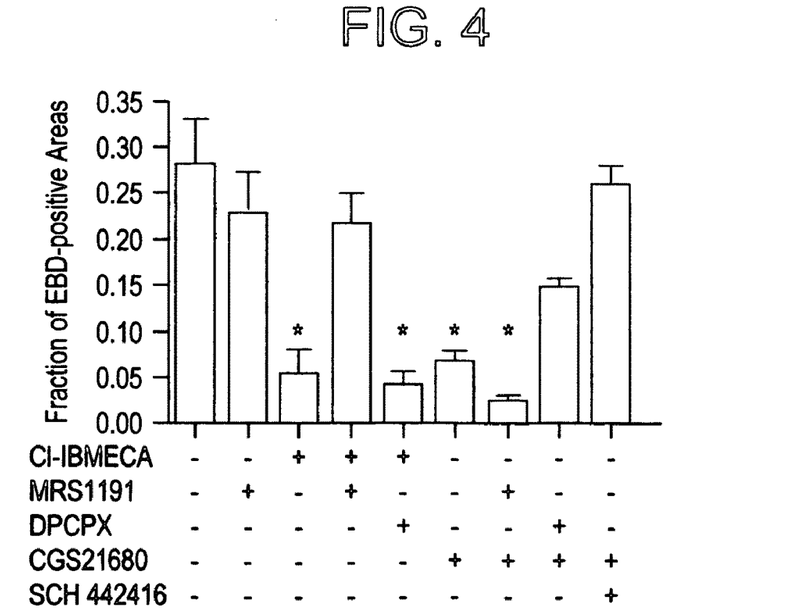
FIG. 4 shows the effects on EBD staining following treatment with Cl-IBMECA or CGS21680 in the presence or the absence of DPCPX, SCH 442416 or MRS1191, determined at the indicated combinations. Average EBD staining (±SE) of skeletal muscle sections following treatment with vehicle or adenosine ligand is shown. $P>0.05$ for comparison between any pair of the following groups: Cl-IBMECA (n=8 mice), DPCPX plus Cl-IBMECA (n=9), CGS21680 (n=9), CGS21680 plus MRS1191 (n=8), CGS21680 plus DPCPX (n=10). * $P<0.05$ for Cl-IBMECA, DPCPX plus Cl-IBMECA, CGS21680, or CGS21680 plus MRS1191 vs. any of the following groups: PBS, MRS1191 (15 mice), CGS21680 plus SCH 442416 (n=5 mice), or MRS1191 plus Cl-IBMECA (n=22) in a Newman-Keuls posttest comparison.

A Novel Anti-ischemic Protective Role of Adenosine $A_3$ Receptors in Skeletal Muscle The $A_3$ receptor agonist Cl-IBMECA induced a significant reduction in EBD-positive cells (FIG. 4; Cl-IBMECA treatment: 5.4%±2.6%, n=8 mice, P<0.05 vs. PBS treatment). This reduction in EBD-positive cells was sensitive to antagonism by MRS1191 (FIG. 4; MRS1191 and Cl-IBMECA treatment: 21.5%±3.5%, n=22 mice, P<0.05 vs. Cl-IBMECA treatment) but not by DPCPX (FIG. 4; DPCPX and Cl-IB-MECA treatment: 4%±1.6%, n=9 mice, P>0.05 vs. Cl-IB-MECA treatment). Neither MRS1191 (23%±4.4%, n=15 mice) nor DPCPX (19.3%±4.4%, n=8 mice) alone had any effect on the extent of ischemia/reperfusion-induced skeletal muscle injury.

Mice pretreated with the adenosine $A_{2A}$ receptor-selective agonist CGS21680 showed reduced muscle injury compared with PBS vehicle-treated animals (6.6%±3.5%, n=9 mice, P<0.05 vs. PBS treatment; FIG. 4). The protective effect of CGS21680 was attenuated by DPCPX (DPCPX and CGS21680 treatment: 14.7%±2.3%, n=10 mice, P>0.05 vs. DPCPX alone). The $A_3$ antagonist MRS1191 could not inhibit the CGS21680-induced skeletal muscle protection (MRS1191 and CGS21680 treatment: 2.4%±1.25%, n=8 mice, P<0.05 vs. MRS1191 alone). The adenosine $A_{2A}$ receptor-selective antagonist SCH 442416 completely abrogated the CGS21680-induced protection (FIG. 4). Animals treated with SCH 442416 and CGS21680 showed significantly larger EBD-positive areas (26%±4%, n=5 mice, SE) than mice treated with CGS21680 alone (P<0.05).

Figure 5:
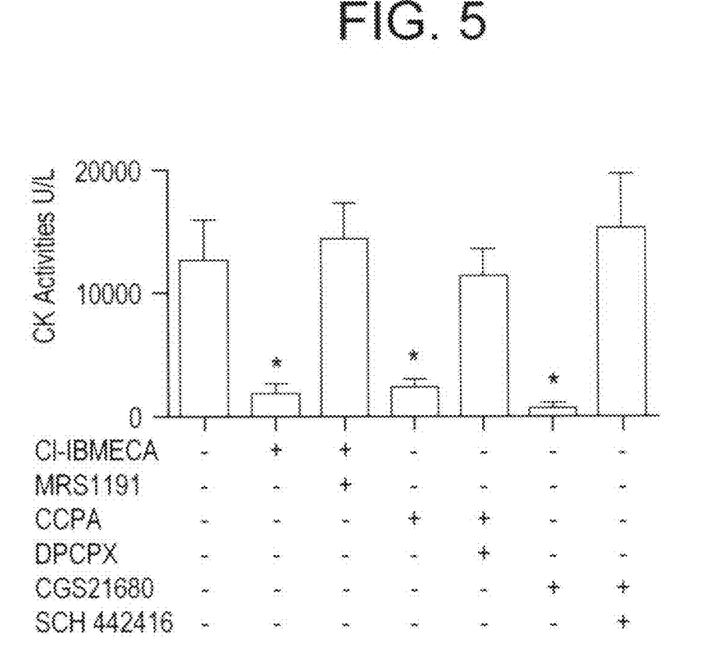
FIG. 5 shows adenosine receptor agonists and antagonists administered as in the experiments described in FIGS. 1-3. CK was used as a marker of muscle injury. * $P<0.05$ for Cl-IBMECA, CCPA or CGS21680 vs. any of the others). Data were mean and standard error of 14 mice (PBS), 13 mice (Cl-IBMECA), 15 mice (MRS1191 plus Cl-IBMECA), 9 mice (DPCPX plus CCPA), and 11 mice (CCPA), 10 mice (CGS21680), 8 mice (CGS21680 plus SCH442416).

CK levels were measured as another method to quantify skeletal muscle injury induced by ischemia and reperfusion. Cl-IBMECA, CGS21680 and CCPA were able to reduce these levels when each agonist was administered individually before ischemia and reperfusion (FIG. 5). CK in Cl-IBMECA-treated mice was 1840 U/L±910 U/L, n=13 mice. In CCPA-treated mice, CK was 2340 U/L±710 U/L, n=11 mice. CK in CGS21680-treated mice was 838 U/L±243 U/L, n=10 mice (P<0.05 for any agonist vs. vehicle-treated mice, which had a serum CK level of 12,600 U/L±3300 U/L, n=14 mice). The protection against CK release induced by $A_1$ $A_{2A}$ or $A_3$ receptors was blocked by an antagonist of each adenosine receptor subtype. In mice treated with MRS1191 and Cl-IBMECA, serum CK was 14,400 U/L±2900 U/L (n=15 mice, P<0.05 vs. Cl-IBMECA alone). Serum CK in mice treated with DPCPX plus CCPA was 11,300 U/L±2200 U/L (n=9 mice, P<0.05 vs. CCPA alone). CK in mice treated with SCH 442416 plus CGS21680 was 15180 U/L±4420 U/L, n=8 mice. The data obtained on serum CK activity, derived from the same method of agonist and antagonist administration in the same ischemia/reperfusion injury model, complement those obtained through EBD staining.

EXAMPLE 3

Specificity of Protection Induced by Each Adenosine Receptor Subtype

Figure 3:
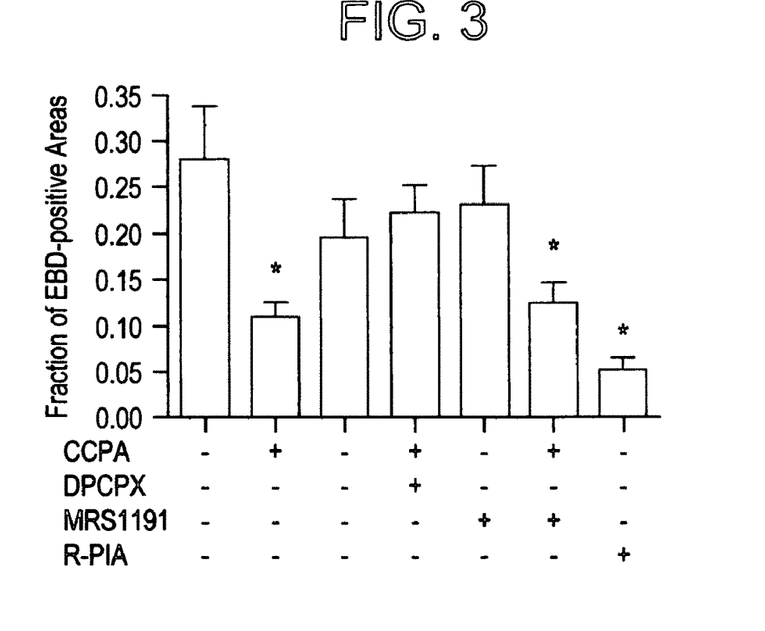
FIG. 3 shows the average EBD staining (±SE) of skeletal muscle sections following treatment with vehicle or adenosine ligand quantified by blinded observers (n=8 mice for DPCPX alone and 15 mice for MRS1191 alone). * $P<0.05$ for CCPA or MRS1191 plus CCPA or R-PIA vs. any of the following groups: treatment with PBS, DPCPX, MRS1191, or CCPA plus DPCPX (Newman-Keuls posttest comparison). $P>0.05$ for any comparison between CCPA, MRS1191 plus CCPA, and R-PIA.
Figure 6:
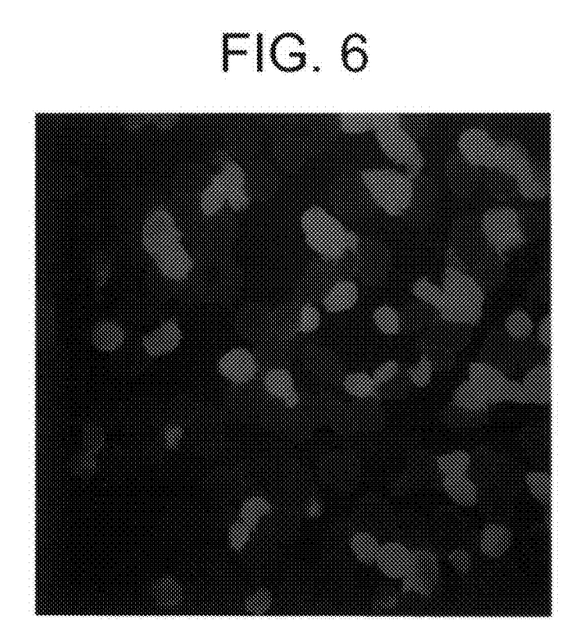
FIG. 6 shows a typical EBD staining in a vehicle-injected PLC β2/β3-null mouse following I/R is shown. The extent of EBD staining was similar to that obtained in vehicle-injected wild-type mice after I/R (see FIG. 3, $P>0.05$).
Figure 7:
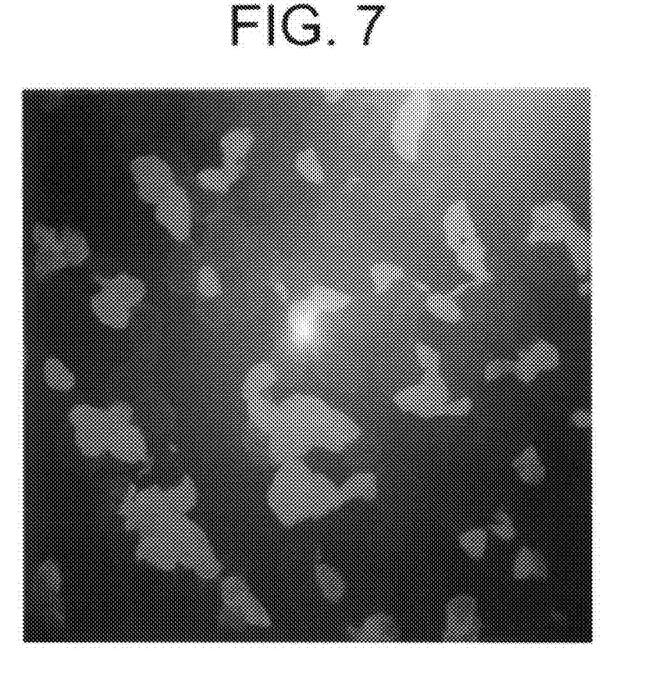
FIG. 7 shows a representative EBD staining in a Cl-IBMECA-treated mouse.
Figure 8:
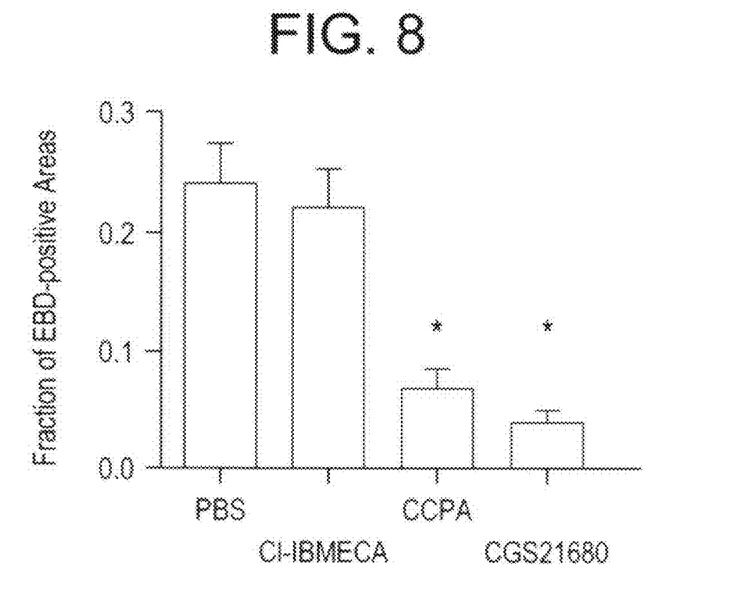
FIG. 8 shows average EBD staining (±SE) of skeletal muscle sections from PLC β2/β3-null mice following treatment with vehicle or adenosine ligand. * $P<0.05$, CCPA, CGS21680 vs. either PBS or Cl-IBMECA. $P>0.05$, PBS vs. Cl-IBMECA; $P>0.05$, CCPA vs. CGS21680.

The specificity by which each adenosine receptor agonist mediates its protective response was further illustrated by testing the effect of the agonist in PLC β2/β3-null mice. Cl-IBMECA-induced protection was completely abrogated in PLC β2/β3-null mice (Cl-IBMECA treatment: 22%±3.6%, n=8 mice, P>0.05 vs. PBS treatment: 23.4%±4%, n=9 mice; FIGS. 6-8), whereas protection induced by CCPA was unaffected (CCPA treatment: 8.5%±2.5%, n=10 mice P<0.05 vs. PBS treatment). PLC β2/β3 deficiency alone had no effect on ischemia/reperfusion-induced skeletal muscle injury (PBS vehicle-treated WT mice had 28%±6% EBD-positive area, n=7; PLC β2/β3-null mice had 23.4%±4% EBD-positive area, n=9, P>0.05; FIG. 3 and FIG. 8, respectively).

The $A_{2A}$ agonist CGS21680 was also able to cause cytoprotection in PLC β2/β3-null mice (CGS21680 treatment: 4%±1.1%, n=6 PLC β2/β3-null mice, P<0.05 vs. PBS treatment: 23.4±4%, n=9 PLC β2/β3-null mice; FIG. 8). Because the $A_{2A}$ receptor is coupled to stimulation of adenylyl cyclase activity and cyclic AMP accumulation, it was not unexpected that the absence of PLC β2/β3 had no effect on the $A_{2A}$ receptor's cytoprotective effect. The cytoprotective action of adenosine $A_{2A}$ receptors in skeletal muscle is independent of and separate from the salutary effect mediated by adenosine $A_1$ or $A_3$ receptors in that tissue.

EXAMPLE 4

Adenosine $A_3$ Receptor Agonist Protection Against Exercise-induced Skeletal Muscle Injury in Wild Type (Wt) Mice, Beta-sarcoglycan-null Mice and PLCβ2/β3-null Mice Wild type (WT), beta-sarcoglycan-deficient, and PLCβ2/β3-null mice were all 8-10 weeks old and have similar body weights. Beta-sarcoglycan-null mice have been developed as a mouse model of limb-girdle muscular dystrophy. PLCβ2/β3-null mice have been used as a model to determine the physiologic role of these enzyme isoforms in mediating the effect of various adenosine receptor subtypes. The 15% downhill treadmill exercise is an established method to cause exertion-related skeletal muscle injury in rodents and has been used to gauge the success of therapy aimed at reducing skeletal muscle injury in mouse models of muscular dystrophy. Mice were exercised to exhaustion and for similar amount of time. EBD staining showed very few EBD-positive muscle fibers in WT mice after physical exertion, likely owing to the limited extent of exertion-induced skeletal muscle injury in normal mice. Thus, only serum CK activity was used to quantify the extent of skeletal muscle injury in these normal WT mice. In the beta-sarcoglycan-null mice, there was already a significant level of skeletal muscle damage at baseline (in the absence of imposed physical exercise, EBD-positive area was 9.7±2.0%, n=28 mice, SE; serum CK was 2363±310, U/L, n=30 mice, SE). Both EBD staining and serum CK were used to quantify the extent of skeletal muscle injury.

Figure 9:
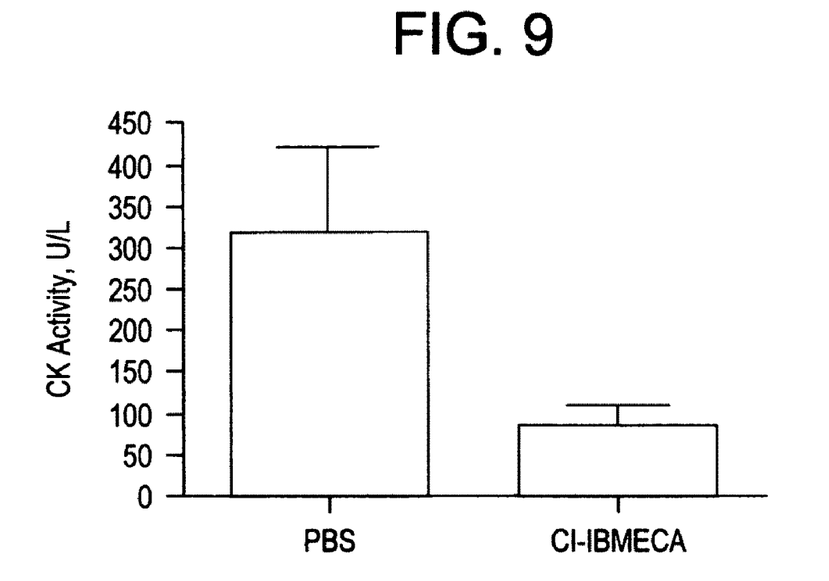
FIG. 9 shows CK levels for adult wild-type mice injected with the $A_3$ receptor agonist Cl-IBMECA and then subjected to exercise.
Figure 10:
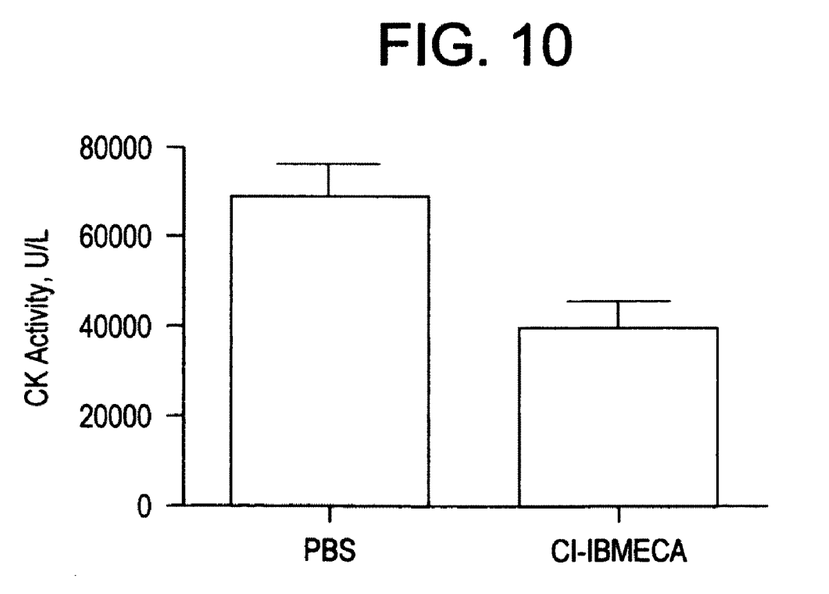
FIG. 10 shows CK levels for beta-sarcoglycan-null mice injected with the $A_3$ receptor agonist Cl-IBMECA and then subjected to exercise.
Figure 11:
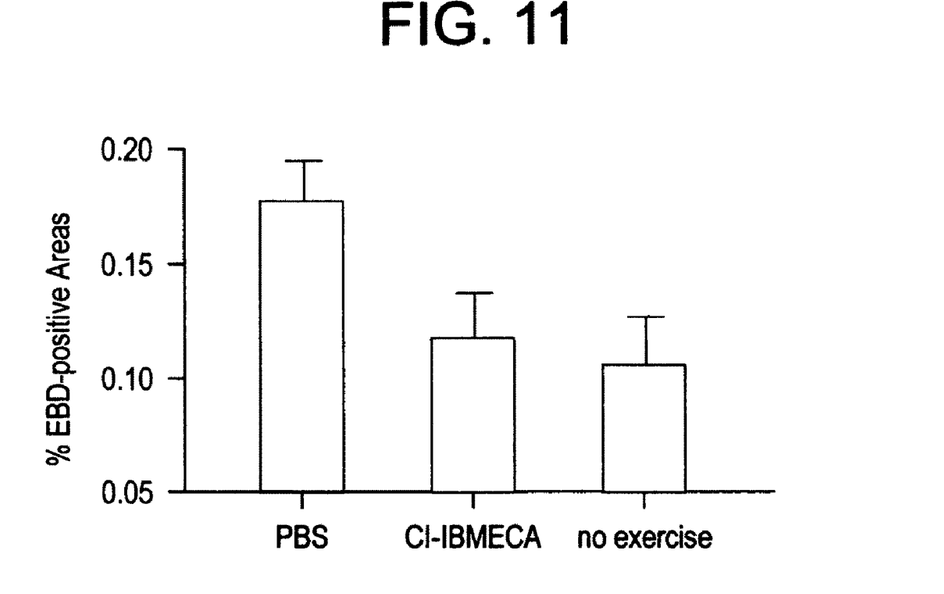
FIG. 11 shows percentage of EBD-stained area for beta-sarcoglycan-null mice injected with the $A_3$ receptor agonist Cl-IBMECA and then subjected to exercise.

Adult wild-type mice were injected with the $A_3$ receptor agonist Cl-IBMECA. They were then subjected to exercise, and their skeletal muscle injuries were quantified using serum CK was used as a marker of muscle injury. (FIG. 9) The $A_3$ receptor agonist Cl-IBMECA caused a reduction in the serum CK as compared to prior treatment with vehicle (0.1% DMSO in sterile phosphate buffered saline or PBS, pH=7.4) (P<0.05, n=11 mice for Cl-IBMECA and n=11 for PBS treatment). Adenosine $A_3$ receptor agonist can protect against exercise-induced skeletal muscle injury in wild type (WT) mice Beta-sarcoglycan-null mice were used as a model of Limb-Girdle Muscular Dystrophy. Mice were treated with Cl-IBMECA and then subjected to exercise. The extent of skeletal muscle injury was determined by (FIG. 10) serum CK level and (FIG. 11) percentage of EBD-stained area. Cl-IBMECA treatment caused a reduction in the serum CK level vs. vehicle treatment (P=0.0066, n=13 mice for both Cl-IBMECA- and PBS treatment groups). Using EBD staining as another index of skeletal muscle injury, Cl-IBMECA treatment also reduced the percentage of EBD-positive area as compared to mice treated with vehicle (P=0.03). Adenosine $A_3$ receptor agonist can protect against exercise-induced skeletal muscle injury in beta-sarcoglycan-null mice.

Figure 12:
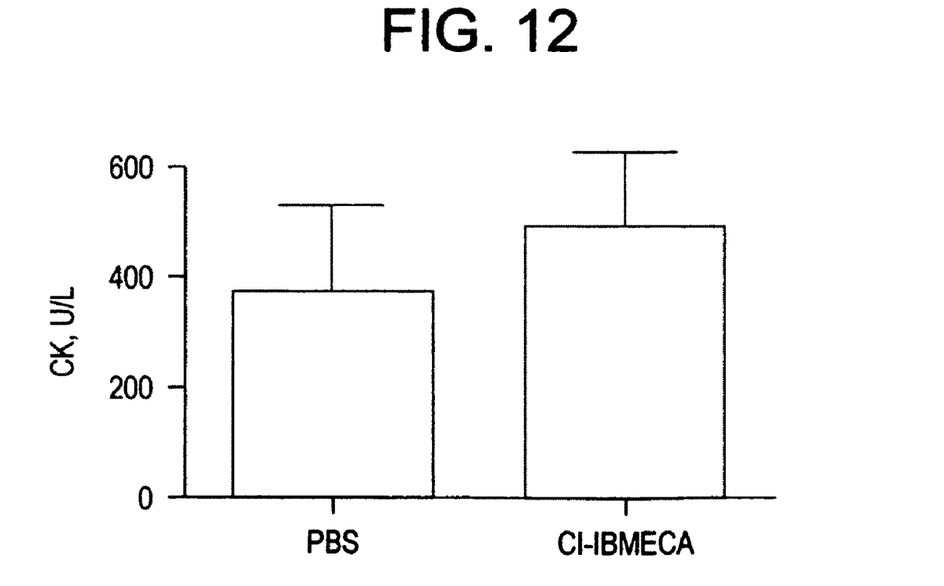
FIG. 12 shows CK levels for PLCβ2/β3-null mice injected with the $A_3$ receptor agonist Cl-IBMECA and then subjected to exercise.

PLCβ2/β3-null mice were used as a model to determine the role of PLCβ2/β3 in mediating the protective effect on exercise-induced injury by Cl-IBMECA. PLCβ2/β3-null mice were treated with PBS or Cl-IBMECA and then subjected to exercise. Serum CK levels were used to quantify the extent of skeletal muscle injury. (FIG. 12) Cl-IBMECA was unable to induce a reduction in the serum CK level (P>0.1, n=8 mice for both PBS and Cl-IBMECA treatment groups). Adenosine $A_3$ receptor agonist was unable to protect against exercise-induced skeletal muscle injury in PLCβ2/β3-null mice.

Several conclusions can be drawn from these results. First, the adenosine receptor agonist Cl-IBMECA, which acts selectively via the $A_3$ receptor, can reduce exertion-induced skeletal muscle injury in WT mice. Second, Cl-IBMECA was also effective in decreasing exertion-induced skeletal muscle injury in beta-sarcoglycan-null mouse model of limb girdle muscular dystrophy, with a reduction in both serum CK level and EBD-stained muscle area. Third, PLCβ2/β3 is an important effector downstream of adenosine $A_3$ receptors and mediates the protection from exertion-related injury, similar to its role in the anti-ischemic protection in the skeletal muscle. Fourth, agonists at adenosine $A_3$ receptors represent a novel class of agents that can ameliorate both ischemia/reperfusion- and exertion-induced skeletal muscle injury. These protective effects can be extended to not only the normal but also diseased subjects. The specific latter example is muscular dystrophy; in the present study, the limb-girdle muscular dystrophy showed rescue of its skeletal muscle injury by Cl-IBMECA.

The unique advantage of the methods disclosed herein is that targeting of the $A_3$ receptor does not cause significant hypotension or bradycardia in mammals. Although $A_1$ and $A_{2A}$ receptors can also exert a protective effect in the same model of ischemia/reperfusion injury, both $A_1$ and $A_{2A}$ receptors can cause cardiodepression. Another unique advantage is that $A_3$ receptor agonists are small molecules that can be injected or absorbed via the GI tract. Because the mechanism by which an $A_3$ receptor agonist achieves skeletal muscle protection is different from that induced by $A_1$ or $A_{2A}$ receptor agonists, the $A_3$ receptor may be uniquely suited as a novel target for skeletal muscle protection.

"Alkyl" includes straight chain, branched, and cyclic saturated aliphatic hydrocarbon groups, having the specified number of carbon atoms, generally from 1 to about 6 carbon atoms for the straight chain and generally from 3 to about 6 carbon atoms for the branched and cyclic. Examples of alkyl include, but are not limited to, methyl, ethyl, n-propyl, iso-propyl, n-butyl, 3-methylbutyl, t-butyl, n-pentyl, sec-pentyl, cyclopentyl, and cyclohexyl.

"Haloalkyl" indicates straight chain, branched, and cyclic alkyl groups having the specified number of carbon atoms, substituted with 1 or more halogen atoms, generally up to the maximum allowable number of halogen atoms ("perhalogenated", e.g. perfluorinated). Examples of haloalkyl include, but are not limited to, trifluoromethyl, difluoromethyl, 2-fluoroethyl, and penta-fluoroethyl.

"Alkoxy" includes an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkoxy" indicates a haloalkyl group as defined above attached through an oxygen bridge.

"Aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, anthracene, pentacene, fluorene, and bi-phenyl.

"Halo" or "halogen" as used herein refers to fluoro, chloro, bromo, or iodo.

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

The terms "a" and "an" herein do not denote a limitation of quantity, but rather denote the presence of at least one of the referenced item.

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. A method of treating skeletal muscle comprising administering to an individual in need of treatment for skeletal muscle injury an effective amount of an adenosine $A_3$ receptor agonist.

2. The method of claim 1, wherein the adenosine $A_3$ receptor agonist is a compound of structure (I) or (II):

(I)

(II)

wherein each occurrence of X is N or CH; $R^1$ is aryl or —($C_1$-$C_3$ alkyl)-aryl wherein each aryl group is optionally substituted with 1, 2, or 3 substituents selected from halogen, $C_1$-$C_6$ alkyl, $C_1$-$C_6$ haloalkyl, —O($C_1$-$C_6$ alkyl), —O($C_1$-$C_6$ haloalkyl), —S($C_1$-$C_6$ alkyl), —S($C_1$-$C_6$ haloalkyl), —OH, —SH, nitro, or cyano; $R^2$ is hydrogen, $C_1$-$C_6$ alkyl, or $C_1$-$C_6$ haloalkyl; $R^3$ is hydrogen, halogen, $C_1$-$C_6$ alkyl, $C_1$-$C_6$ haloalkyl, —O($C_1$-$C_6$ alkyl), —O($C_1$-$C_6$ haloalkyl), —S($C_1$-$C_6$ alkyl), —S($C_1$-$C_6$ haloalkyl), —OH, or —SH; $R^4$ is hydrogen, halogen, $C_1$-$C_6$ alkyl, or $C_1$-$C_6$ haloalkyl; $R^5$ —(C=O)$NR^7R^8$, —(C=S)$NR^7R^8$, —O(C=O)$NR^7R^8$, —$NR^9$(C=O)$NR^7R^8$, —O(C=S)$NR^7R^8$, or —$NR^9$(C=S)$NR^7R^8$ wherein $R^7$ is hydrogen, $C_1$-$C_6$ alkyl, or $C_1$-$C_6$ haloalkyl, $R^8$ is hydrogen, $C_1$-$C_6$ alkyl, or $C_1$-$C_6$ haloalkyl, or $R^7$ and $R^8$ combine to form a cyclic structure having 3, 4, or 5 carbons and 0, 1, or 2 heteroatoms of oxygen or $NR^{10}$, $R^{10}$ is hydrogen or $C_1$-$C_6$ alkyl, and $R^9$ is hydrogen or $C_1$-$C_6$ alkyl; and each occurrence of $R^6$ independently is hydrogen, $C_1$-$C_6$ alkyl, $C_1$-$C_6$ haloalkyl, or —(C=O)$C_1$-$C_6$ alkyl.

3. The method of claim 1, wherein the adenosine $A_3$ receptor agonist is an agonist of structure (III) or (IV)

wherein each occurrence of X is N or CH; $R^1$ is aryl or —($C_1$-$C_3$ alkyl)-aryl wherein each aryl group is optionally substituted with 1, 2, or 3 substituents selected from halogen, $C_1$-$C_6$ alkyl, $C_1$-$C_6$ haloalkyl, —O($C_1$-$C_6$ alkyl), —O($C_1$-$C_6$ haloalkyl), —S($C_1$-$C_6$ alkyl), —S($C_1$-$C_6$ haloalkyl), —OH, —SH, nitro, or cyano; $R^2$ is hydrogen, $C_1$-$C_6$ alkyl, or $C_1$-$C_6$ haloalkyl; $R^3$ is hydrogen, halogen, $C_1$-$C_6$ alkyl, $C_1$-$C_6$ haloalkyl, —O($C_1$-$C_6$ alkyl), —O($C_1$-$C_6$ haloalkyl), —S($C_1$-$C_6$ alkyl), —S($C_1$-$C_6$ haloalkyl), —OH, or —SH; $R^4$ is hydrogen, halogen, $C_1$-$C_6$ alkyl, or $C_1$-$C_6$ haloalkyl; $R^5$ is —(C=O)$NR^7R^8$, —(C=S)$NR^7R^8$, —O(C=O)$NR^7R^8$, —$NR^9$(C=O)$NR^7R^8$, —O(C=S)$NR^7R^8$, or —$NR^9$(C=S)$NR^7R^8$ wherein $R^7$ is hydrogen, $C_1$-$C_6$ alkyl, or $C_1$-$C_6$ haloalkyl, $R^8$ is hydrogen, $C_1$-$C_6$ alkyl, or $C_1$-$C_6$ haloalkyl, or $R^7$ and $R^8$ combine to form a cyclic structure having 3, 4, or 5 carbons and 0, 1, or 2 heteroatoms of oxygen or $NR^{10}$, $R^{10}$ is hydrogen or $C_1$-$C_6$ alkyl, and $R^9$ is hydrogen or $C_1$-$C_6$ alkyl; and each occurrence of $R^6$ independently is hydrogen, $C_1$-$C_6$ alkyl, $C_1$-$C_6$ haloalkyl, or —(C=O)$C_1$-$C_6$ alkyl.

4. The method of claim 3, wherein X is N; $R^1$ is phenyl or benzyl wherein the phenyl or benzyl group is optionally substituted with 1, 2, or 3 substituents selected from halogen, $C_1$-$C_6$ alkyl, or $C_1$-$C_6$ haloalkyl; $R^2$ is hydrogen; $R^3$ is hydrogen or halogen; $R^4$ is hydrogen; $R^5$ is —(C=O)$NR^7R^8$, wherein $R^7$ is hydrogen, $C_1$-$C_6$ alkyl, or $C_1$-$C_6$ haloalkyl and $R^8$ is hydrogen; and $R^6$ is hydrogen.

5. The method of claim 2, wherein the adenosine $A_3$ receptor agonist is $N^6$-(3-iodobenzyl)adenosine-5'-N-methyluronamide; 2-chloro-$N^6$-(3-iodobenzyl)adenosine-5'-N-methyluronamide; (1'R,2'R,3'S,4'R,5'S)-4-{2-chloro-6-[(3-chlorophenylmethyl)amino]purin-9-yl}-1-(methylaminocarbonyl)bicyclo[3.1.0]hexane-2,3-diol; $N^6$-(3-chlorobenzyl)adenosine-5'-N-methyluronamide; 2-chloro-$N^6$-(3-chlorobenzyl)adenosine-5'-N-methyluronamide; $N^6$-(3-fluorobenzyl)adenosine-5'-N-methyluronamide; 2-chloro-$N^6$-(3-fluorobenzyl)adenosine-5'-N-methyluronamide; $N^6$-(3-methylbenzyl)adenosine-5'-N-methyluronamide; 2-chloro-$N^6$-(3-methylbenzyl)adenosine-5'-N-methyluronamide; $N^6$-(3-nitrobenzyl)adenosine-5'-N-methyluronamide; 2-chloro-$N^6$-(3-nitrobenzyl)adenosine-5'-N-methyluronamide; $N^6$-(3-cyanobenzyl)adenosine-5'-N-methyluronamide; 2-chloro-$N^6$-(3-cyanobenzyl)adenosine-5'-N-methyluronamide; $N^6$-(3,5-dichlorobenzyl)adenosine-5'-N-methyluronamide; 2-chloro-$N^6$-(3,5-dichlorobenzyl)adenosine-5'-N-methyluronamide; $N^6$-(3,5-diiodobenzyl)adenosine-5'-N-methyluronamide; 2-chloro-$N^6$-(3,5-diiodobenzyl)adenosine-5'-N-methyluronamide; $N^6$-(3,5-difluorobenzyl)adenosine-5'-N-methyluronamide; 2-chloro-$N^6$-(3,5-difluorobenzyl)adenosine-5'-N-methyluronamide; $N^6$-(3,5-dimethylbenzyl)adenosine-5'-N-methyluronamide; 2-chloro-$N^6$-(3,5-dimethylbenzyl)adenosine-5'-N-methyluronamide; $N^6$-(3-iodophenyl)adenosine-5'-N-methyluronamide; 2-chloro-$N^6$-(3-iodophenyl)adenosine-5'-N-methyluronamide; $N^6$-(3-chlorophenyl)adenosine-5'-N-methyluronamide; 2-chloro-$N^6$-(3-chlorophenyl)adenosine-5'-N-methyluronamide; $N^6$-(3-fluorophenyl)adenosine-5'-N-methyluronamide; 2-chloro-$N^6$-(3-fluorophenyl)adenosine-5'-N-methyluronamide; $N^6$-(3-methylphenyl)adenosine-5'-N-methyluronamide; 2-chloro-$N^6$-(3-methylphenyl)adenosine-5'-N-methyluronamide; $N^6$-(3-nitrophenyl)adenosine-5'-N-methyluronamide; 2-chloro-$N^6$-(3-nitrophenyl)adenosine-5'-N-methyluronamide; $N^6$-(3-cyanophenyl)adenosine-5'-N-methyluronamide; 2-chloro-$N^6$-(3-cyanophenyl)adenosine-5'-N-methyluronamide; $N^6$-(3,5-dichlorophenyl)adenosine-5'-N-methyluronamide; 2-chloro-$N^6$-(3,5-dichlorophenyl)adenosine-5'-N-methyluronamide; $N^6$-(3,5-diiodophenyl)adenosine-5'-N-methyluronamide; 2-chloro-$N^6$-(3,5-diiodophenyl)adenosine-5'-N-methyluronamide; $N^6$-(3,5-difluorophenyl)adenosine-5'-N-methyluronamide; 2-chloro-$N^6$-(3,5-difluorophenyl)adenosine-5'-N-methyluronamide; $N^6$-(3,5-dimethylphenyl)adenosine-5'-N-methyluronamide; 2-chloro-$N^6$-(3,5-dimethylphenyl)adenosine-5'-N-methyluronamide, or a combination comprising one or more of the foregoing adenosine $A_3$ receptor agonists.

6. The method of claim 1, wherein the individual is at risk of, or has been diagnosed with, a skeletal muscle ischemia and reperfusion injury.

7. The method of claim 6, wherein the individual has undergone, or is expected to undergo, a surgical operation.

8. The method of claim 7, wherein the individual has undergone, or is expected to undergo, a plastic surgical operation, a vascular surgical operation, or reconstructive surgical operation where there is a risk of ischemia and reperfusion injury.

9. The method of claim 1, wherein the individual is participating in, expected to participate in, exercise.

10. The method of claim 9, wherein the exercise is strenuous exercise.

11. The method of claim 1, wherein the individual is suffering from a disease that affects skeletal muscle.

12. The method of claim 11, wherein the disease that affects skeletal muscle is a degenerative muscle disease.

13. The method of claim 12, wherein the degenerative muscle disease is inclusion body myositis, a muscular dystrophy, or Amyotrophic Lateral Sclerosis.

14. The method of claim 1, wherein the individual is an older subject suffering from a decrease in skeletal muscle function due to aging-related susceptibility to ischemia and reperfusion or physical exertion-related injury.

15. A method of protecting skeletal muscle comprising
administering to an individual in need of treatment for exertion-related skeletal muscle injury an effective amount of an adenosine $A_3$ receptor agonist.

16. The method of claim 15, wherein the individual is a healthy individual.

17. The method of claim 15, wherein the individual is suffering from a disease that affects skeletal muscle.

18. The method of claim 17, wherein the disease that affects skeletal muscle is a degenerative muscle disease.

19. The method of claim 18, wherein the degenerative muscle disease is inclusion body myositis, a muscular dystrophy, or Amyotrophic Lateral Sclerosis.

20. A method of preconditioning skeletal muscles from ischemia and reperfusion injury or for exertion-related skeletal muscle injury comprising
administering to an individual in need of treatment for ischemia and reperfusion injury or for exertion-related skeletal muscle injury an effective amount of an adenosine $A_3$ receptor agonist.

21. The method of claim 20, wherein the adenosine $A_3$ receptor agonist is administered to an individual at risk of ischemia/reperfusion injury or for exertion-related skeletal muscle injury.

* * * * *